US011406489B2

(12) United States Patent
Simmons

(10) Patent No.: US 11,406,489 B2
(45) Date of Patent: Aug. 9, 2022

(54) IMPLANT WITH FIDUCIAL MARKERS

(71) Applicant: Cornell University, Ithaca, NY (US)

(72) Inventor: Rache Simmons, New York, NY (US)

(73) Assignee: Cornell University, Ithaca, NY (US)

(*) Notice: Subject to any disclaimer, the term of this patent is extended or adjusted under 35 U.S.C. 154(b) by 86 days.

(21) Appl. No.: 17/065,157

(22) Filed: Oct. 7, 2020

(65) Prior Publication Data

US 2022/0125574 A1 Apr. 28, 2022

Related U.S. Application Data

(60) Provisional application No. 62/911,682, filed on Oct. 7, 2019.

(51) Int. Cl.
*A61B 90/00* (2016.01)
*A61F 2/12* (2006.01)
*A61L 27/52* (2006.01)

(52) U.S. Cl.
CPC ............... *A61F 2/12* (2013.01); *A61L 27/52* (2013.01); *A61F 2210/00* (2013.01); *A61F 2250/0098* (2013.01)

(58) Field of Classification Search
CPC .............. A61F 2/12; A61F 2210/00; A61F 2250/0098; A61L 27/52; A61B 90/39–2090/3995
See application file for complete search history.

(56) References Cited

U.S. PATENT DOCUMENTS

| | | | |
|---|---|---|---|
| 7,792,569 B2 | 9/2010 | Burbank et al. | |
| 8,064,987 B2 | 11/2011 | Carr, Jr. | |
| 8,470,294 B2 | 6/2013 | Kaplan | |
| 9,352,071 B2 | 5/2016 | Landgrebe et al. | |
| 10,071,173 B2 | 9/2018 | Maiorano et al. | |
| 10,123,862 B2 | 11/2018 | Landgrebe et al. | |
| 2003/0010929 A1 | 1/2003 | Priewe et al. | |
| 2005/0234336 A1* | 10/2005 | Beckman | A61B 90/39 600/431 |
| 2008/0058640 A1 | 3/2008 | Jones et al. | |
| 2009/0088635 A1* | 4/2009 | Fisher | A61B 90/39 600/437 |
| 2009/0131825 A1 | 5/2009 | Burbank et al. | |
| 2009/0259125 A1 | 10/2009 | Stinson | |

(Continued)

FOREIGN PATENT DOCUMENTS

| | | | |
|---|---|---|---|
| EP | 2840965 B1 | 4/2020 | |
| WO | WO-2019/126794 A1 | 6/2019 | |

OTHER PUBLICATIONS

Gautreau, Z, et al Characterizing Viscoelastic Properties of Polyacrylamide Gels (2006) Worcester Polytechnic Institute: Major Qualifying Project Report (Year: 2006).*

(Continued)

*Primary Examiner* — Brian A Dukert
*Assistant Examiner* — Rebecca Lynee Zimmerman
(74) *Attorney, Agent, or Firm* — Schwegman Lundberg & Woesner, P.A.

(57) ABSTRACT

An implant can include a flexible body made of a non-bioresorbable hydrogel material. The implant can also include a radiopaque marker located within the flexible body, where the body and the radiopaque marker can be implanted in a body cavity to mark the cavity in a radiographic image of the cavity.

12 Claims, 7 Drawing Sheets

(56) References Cited

U.S. PATENT DOCUMENTS

| | | |
|---|---|---|
| 2014/0051996 A1 | 2/2014 | Sirimanne et al. |
| 2014/0156003 A1 | 6/2014 | Corbitt et al. |
| 2014/0239528 A1 | 8/2014 | Govil et al. |
| 2016/0128797 A1 | 5/2016 | Burbank et al. |
| 2017/0218228 A1 | 8/2017 | Jose et al. |
| 2019/0008606 A1 | 1/2019 | Ahn |
| 2019/0029560 A1 | 1/2019 | Harmer et al. |
| 2019/0076212 A1 | 3/2019 | Liu |
| 2019/0201160 A1* | 7/2019 | Hornscheidt .......... A61B 90/39 |
| 2019/0282325 A1* | 9/2019 | Alvarez ................ A61B 90/39 |
| 2019/0358468 A1 | 11/2019 | Stubbs et al. |

OTHER PUBLICATIONS

"BioZorb® 3D Bioabsorbable Marker", [online]. © Copyright 2021 Hologic, Inc. [retrieved on Jan. 7, 2021]. Retrieved from the Internet: <URL: https://www.hologic.com/hologic-products/breast-skeletal/biozorbr-3d-bioabsorbable-marker>, (2021), 4 pgs.

* cited by examiner

FIG. 7A  FIG. 7B

IMPLANT WITH FIDUCIAL MARKERS

CLAIM OF PRIORITY

This patent application claims the benefit of priority, under 35 U.S.C. Section 119(e), to Simmons U.S. Patent Application Ser. No. 62/911,682, entitled "BIORESORBABLE IMPLANT WITH FIDUCIAL MARKERS," filed on Oct. 7, 2019, which is hereby incorporated by reference herein in its entirety.

BACKGROUND

Patients with breast cancer may elect to undergo treatment to treat the lump or tumor. Treatment options include a mastectomy, a lumpectomy, radiation, and chemotherapy depending on several factors, such as size and location of the tumor. In some cases, patients may undergo multiple treatments to improve likelihood of survival. For example, a patient may undergo a lumpectomy procedure, followed by focused radiation therapy. It may also be desirable to monitor tissue of the breast at or near the surgical site, such as at a cavity or void created by removal of a tumor.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7A illustrates a front view of a lumpectomy procedure, in accordance with at least one example of this disclosure.

FIG. 7B illustrates a side view of a lumpectomy procedure, in accordance with at least one example of this disclosure.

DETAILED DESCRIPTION

In a lumpectomy operation, a tumor or cancerous mass can be removed from a breast of a patient, such as by creating an incision to access the tumor. The tumor can be resected, such as by using a scalpel, from the surrounding healthy breast tissue. Some surrounding breast tissue can also be resected to create a margin around the tumor. The combined tissue and tumor resections can create a cavity in the breast tissue.

This cavity can be a target for future radiation therapy where radiation can be directed at the cavity to treat any cancer cells that may remain following resection of the tumor. Implants can be used to demark the cavity for radiographic image guided radiation therapy. That is, an implant can be implanted in the cavity, where the implant can include portions made of radiopaque materials (materials with a relatively high radiodensity). The radiopaque materials can operate as fiducials to guide the radiation therapy. However, some implants can be relatively rigid, which can be palpable to the patient, which can increase patient anxiety. Further, relatively rigid implants can make a patient uncomfortable. Moreover, relatively rigid structures that are bioresorbable can break into many parts, which can be sharp, further creating patient discomfort.

This disclosure can help to address these problems by providing an implant that is relatively flexible. The implant can be generally shaped like a ribbon and can include a fiducial (radiopaque) marker extending along a length of the ribbon. The implant can be configured to be packed into the cavity to fill the cavity, which can help keep the cavity open to improve aesthetics of the breast and can help promote fluid intake into the cavity to help permanently fill the cavity. Also, because the ribbon can be relatively flexible, the implant can be used to fill cavities having irregular shapes. Such flexibility of the ribbon can also allow for the implant to have a reduced palpability, helping to reduce patient anxiety and patient comfort. The flexibility can also reduce a possibility of breaking of the implant into sharp pieces, which can further help improve patient comfort.

In some examples, the ribbon can be bioresorbable such that the fiducial (radiopaque wire) can be left behind after resorption of the ribbon, allowing detection of the cavity following resorption. Further, because the ribbon can have a relatively small thickness, the ribbon can be resorbed by the body in a relatively small period of time. Also, the implant can be provided at one or more lengths, such that the implant can be trimmed to a desired length depending on a size of the cavity.

The above discussion is intended to provide an overview of subject matter of the present patent application. It is not intended to provide an exclusive or exhaustive explanation of the invention. The description below is included to provide further information about the present patent application.

Figure 1:
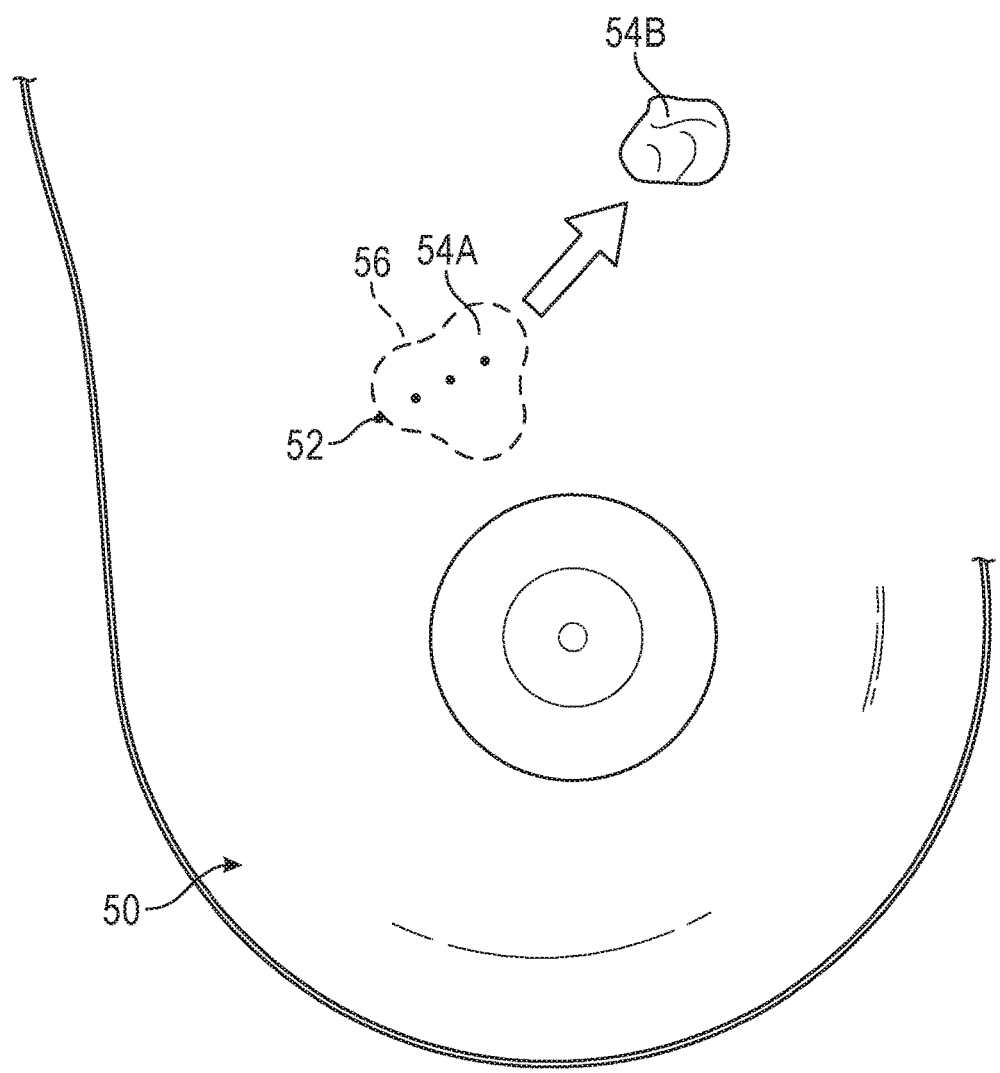
FIG. 1 illustrates a front view of a lumpectomy procedure, in accordance with at least one example of this disclosure.

FIG. 1 illustrates a front view of a lumpectomy operation, in accordance with at least one example of this disclosure. FIG. 1 shows a human breast 50, an incision. 52, a tumor (54A and 54B), and a cavity 56.

In one example, it may be desired to remove the tumor 54A from within the breast 50. In a lumpectomy operation to remove the tumor 54A, the incision 52 can be created on the breast 50, such as by using a scalpel. Using the incision 52 to access the tumor 54B, the tumor 54B can be resected and removed from the breast 50. Before or during removal of the tumor 54 from the breast 50, some surrounding breast tissue can also be resected to create a margin around the tumor 54. Removal of the tumor 54B from the breast 50 (and margin creation) can create the cavity 56 within the breast 50. The cavity 56 can be a target for future radiation therapy where radiation can be directed at the cavity 56 to treat any cancerous (or pre-cancerous) cells that may remain following resection and removal of the tumor 54B. It can be helpful to fill the cavity 56 with a fiducial or marker to act as a radiopaque target for future radiation therapy of the cavity 56 and the surrounding area.

Figure 2:
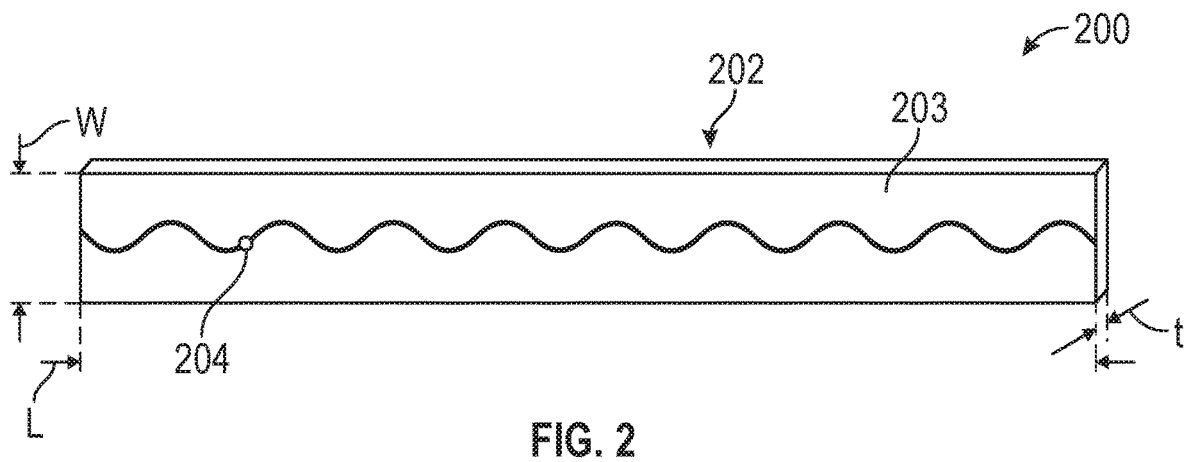
FIG. 2 illustrates a top view of an implant, in accordance with at least one example of this disclosure.

FIG. 2 illustrates a top view of an implant 200, in accordance with at least one example of this disclosure. The implant 200 can include a ribbon 202, and a wire 204.

The implant 200 can generally be an implant configured for implantation into a human body, such as the cavity 56 of the breast 50 of FIG. 1. The implant 200 can be comprised of biocompatible materials, as discussed below in further detail. The ribbon 202 of the implant 200 can be a generally flexible elongate body 203 that can be comprised of a bioresorbable material (can be configured to be broken down and absorbed by a human body). In some examples, the ribbon 202 can be comprised of one or more of a collagen, a glycosaminoglycan, a starch, a silk, an alginate, a chitin, a chitosan, a polylactic acid, a polyglycolic acid, a polyanhydride, a polycaprolactone, a poly(hydroxbutyrate), a poly (hydroxyvalerate), or the like. The ribbon 202 can have one or more layers of the same material or of different materials.

FIG. 2 shows a length L of the implant 200, a width W of the implant 200, and a thickness t of the implant 200. The dimensions of the implant 200 can generally be configured for implantation into a cavity, such as the cavity 56 of the breast 50 of FIG. 1. For example, the width W can be smaller than the length L and the thickness t can be smaller than the width such that the ribbon 202 is generally long, thin, and flexible. In some examples, the width W can be between 0.1 centimeters and 5 centimeters. In some examples, the width W can be between 1 centimeter and 3 centimeters. In some examples, the thickness t can be between 0.01 millimeters and 10 millimeters. In some examples, the thickness can be between 0.05 millimeters and 3 millimeters. Because the ribbon 202 can have a relatively small thickness t, the ribbon 202 can be configured to be resorbed by the body in a relatively small period of time.

The wire 204 can generally be a long thin wire configured for implantation into a cavity. The wire 240 can be connected to the ribbon 202 and can extend along the length L of the ribbon 202. In some examples, the wire 204 can be connected to the ribbon 202 via a bioresorbable adhesive. In some examples, the wire 204 can be woven through the ribbon 202. The wire 204 can be attached to the ribbon 202 in other ways, such as through the use of fasteners, or the like.

The wire 204 can undulate along the length L of the ribbon in some examples, (such as along a sine wave pattern). In other examples, the wire 204 can be straight along the length L (or substantially straight). As shown in FIG. 2, the wire can extend along an entirety of the length L of the ribbon 202. However, in other examples, the wire 204 can extend along only a portion of the length L of the ribbon 202 or can be segmented along the length L of the ribbon 202.

The wire 204 can be made of biocompatible and radiopaque materials such as one or more of titanium, titanium alloys, polyether ether ketone, a stainless-steel alloy, a cobalt-chromium alloy, or the like. The wire 204 can be configured to act as a fiducial or marker for the cavity, such as by being a radiopaque wire visible in radiographic images to mark the cavity after implantation of the implant 200. Further, the wire 204 can act as a fiducial or marker in radiographic images and after resorption of the ribbon 202. Because the ribbon 202 can be bioresorbable, the wire can operate as a fiducial or marker after resorption of the ribbon 202, allowing detection of the cavity following resorption of the ribbon 202.

Figure 3:
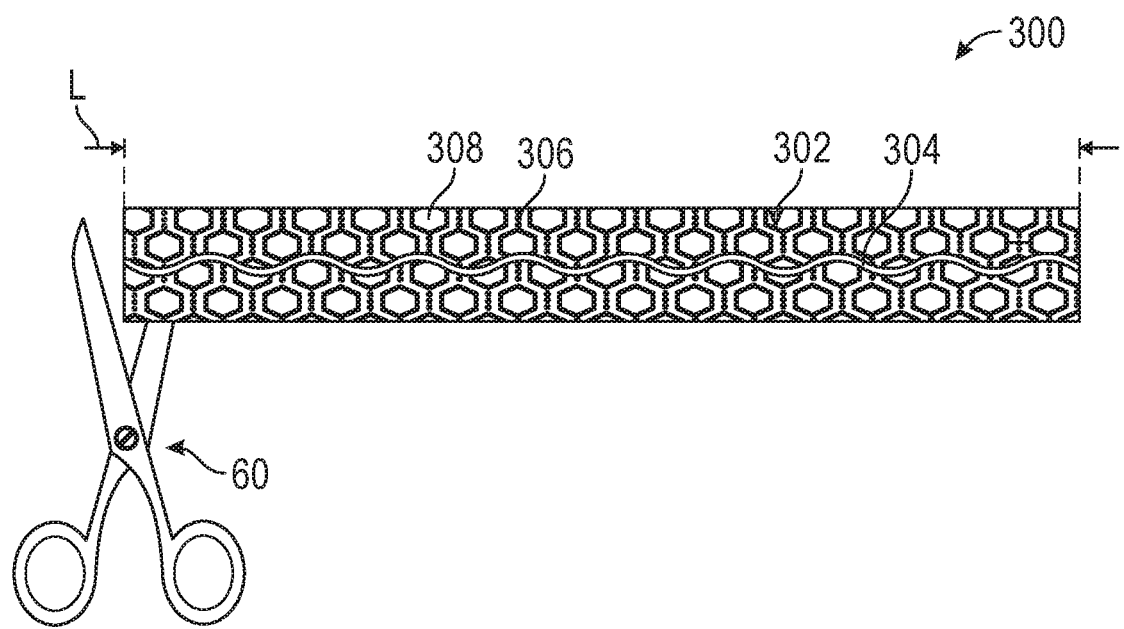
FIG. 3 illustrates a top view of an implant, in accordance with at least one example of this disclosure.

FIG. 3 illustrates a top view of an implant 300, in accordance with at least one example of this disclosure. The implant 300 can include a ribbon 302 and a wire 304. The ribbon 302 can include strands 306 defining openings 308. Also shown in FIG. 3 is a cutting instrument 60.

The implant 300 can be similar to the implant 200 discussed above, except that the ribbon 302 of the implant 300 can be a mesh. The mesh of the ribbon 302 can be made of the strands 306 which can be interconnected to each other and can define openings 308 between the strands 306. The mesh can be of a simple pattern, such as a woven cross pattern, or the like. In some examples, the mesh can have an intricate pattern defining oval openings, hexagonal openings, octagonal openings, or the like. In some examples, the ribbon 302 can be a non-woven mesh (a body including evenly spaced openings).

FIG. 3 also shows that the implant 300 can be trimmed. For example, during a procedure, an implant having a length L can be selected for implantation.

In one example, the length L can be 50 centimeters. During a procedure, it may be determined that the 50 centimeters length is too long. The implant 300 can be trimmed using the cutting instrument 60, which can be a pair of scissors, to achieve a desired length of the implant 300, such as 30 centimeters. In some examples, the length L can be trimmed prior to the procedure. In further examples, the implant 300 can be provided in a large roll and the implant 300 can be cut to a desired length.

The length L can be between 10 centimeters and 10 meters in some examples. The length L can be between 10 centimeters and 1 meter in some examples.

Figure 4:
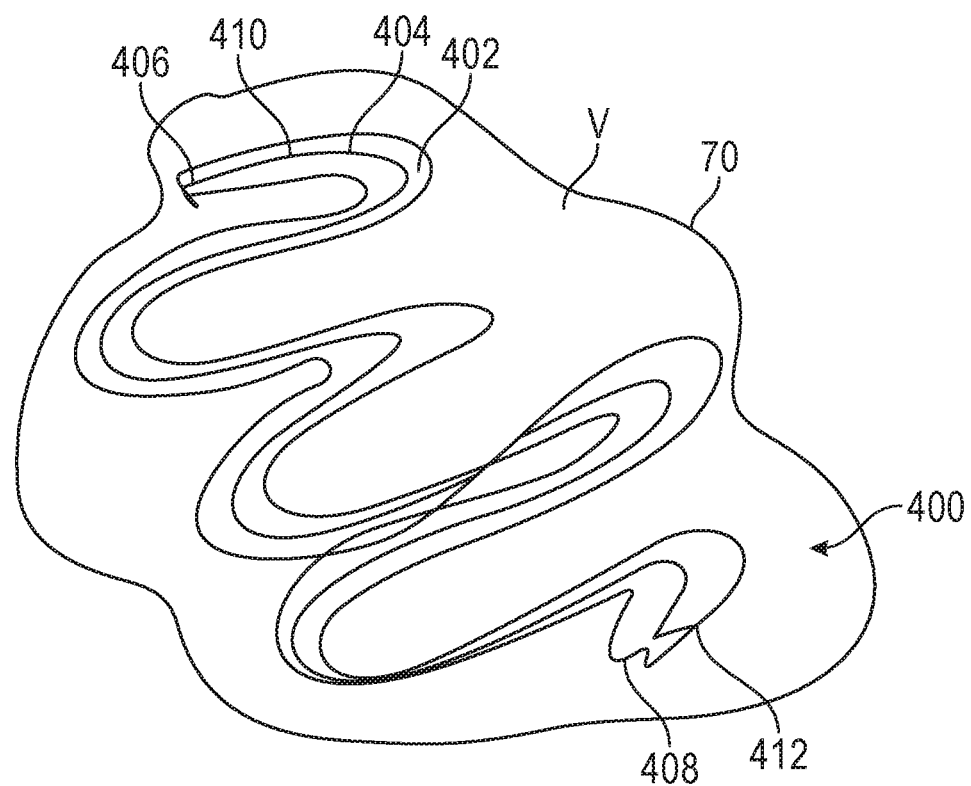
FIG. 4 illustrates a front view of a cavity filled with an implant, in accordance with at least one example of this disclosure.

FIG. 4 illustrates a front view of a cavity 70 filled with an implant 400, in accordance with at least one example of this disclosure. The implant 400 can include a ribbon 402, a wire 404, a first ribbon end 406, a second ribbon end 408, a first wire end 410, and a second wire end 412. FIG. 4 also shows the cavity 70 having a volume V.

The implant 400 can be similar to the implants 100 or 200 discussed above; however, FIG. 4 shows the implant 400 following insertion into the cavity 70. The implant 400 can be inserted into the cavity using various procedures. In one such example, the implant 400 can be selected to have an implant length based on a size of the cavity 70, such as the volume V of the cavity 70. Then, the implant 400 can be trimmed, if desired, based on the volume V of the cavity 70 (similar to the process shown in FIG. 3).

The implant 400 can then be inserted into the cavity 70 (for example using forceps and/or by hand) and can be packed to fill (or at least partially fill) the volume V of the cavity. In some examples, excess portions of the implant 400 can be trimmed following insertion of the implant 400 into the cavity. Following the procedure, an image of the cavity can be acquired, where the image shows the radiopaque wire 404 of the implant within the cavity 70, such that the wire 404 can demark the cavity 70. Following imaging, radiation can be directed at the wire 404 to deliver radiation to the cavity 70.

In some examples, the cavity 70 can have an irregular shape, as shown in FIG. 4. Because the ribbon 402 and the wire 404 are relatively flexible, the implant 400 can be packed into the cavity 70 to substantially (practically) fill the volume V of the cavity 70. Filling of the cavity 70 with the implant 400 can help keep the cavity open post-operatively to help reduce breast indentations, which can improve aesthetics of the breast following the lumpectomy procedure. Keeping the cavity 70 open post-operatively can also help promote fluid intake into the cavity 70 to help promote healing and tissue ingrowth to help permanently fill the cavity 70 (following resorption of the ribbon 402).

Also, because the ribbon 402 and the wire 404 are relatively flexible, the implant 400 can help to reduce palpability of the implant 400, helping to reduce patient anxiety. Also, because the ribbon 402 and the radiopaque wire 404 are configured to flex within the cavity after implantation, the implant 400 can flex or move within the cavity (after implantation) in response to forces applied to the cavity. This can help reduce a painful interaction between the implant 400 and surrounding breast tissue.

In some examples, the first end 406 of the ribbon 402 and the first end 410 of the wire 404 can be configured to move with respect to the second end 408 of the ribbon 402 and the second end 412 of the wire 404 within the cavity 70 (after implantation) in response to forces applied to the cavity 70. This can help reduce a painful interaction between the implant 400 and surrounding breast tissue. In some examples, the first end of the wire 410 and/or the second end of the wire 412 can be rounded or capped to decrease sharpness of the ends 410 and 412 of the wire, which can further help decrease patient discomfort.

Figure 5A:
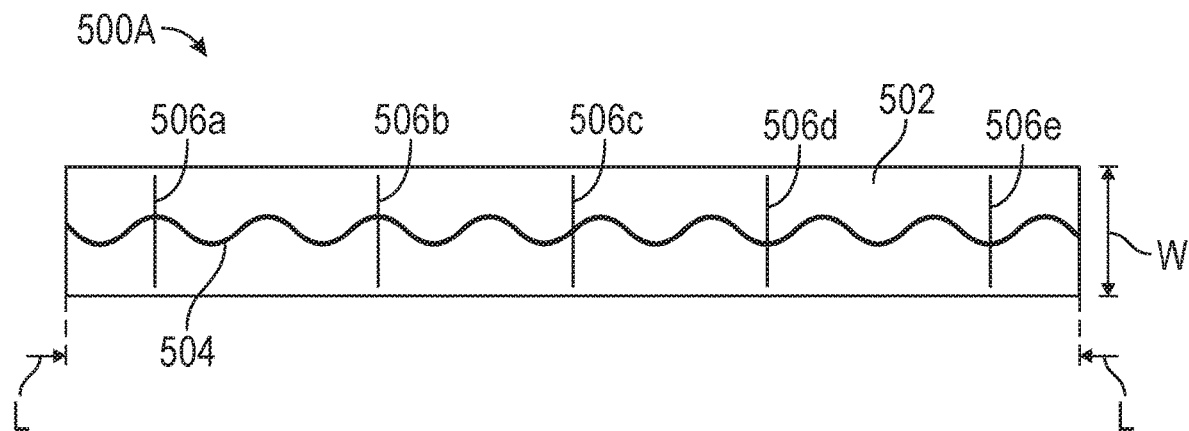
FIG. 5A illustrates a front view of an implant, in accordance with at least one example of this disclosure.

FIG. 5A illustrates a front view of an implant 500A, in accordance with at least one example of this disclosure. The implant 500A can include a ribbon 502, a first wire 504, and second wires 506.

The implant 500A can be similar to the implants discussed above, except that the implant 500A can include the second wires 506, which can be connected to the ribbon 502 and can extend along a width W of an elongate body (the ribbon 502), where the second wires 506 can be oriented substantially orthogonal to the first wire 504. Each of the first wire 504 and the second wires 506 can be radiopaque. Though five of second wires 506 are shown in FIG. 5A, more or less can be used, such as 1, 2, 3, 4, 6, 7, 8, 9, 10, 15, 20, or the like second wires. In some examples, the second wires 506 can be spaced every half centimeter, ever centimeter, every two centimeters, or the like.

Figure 5B:
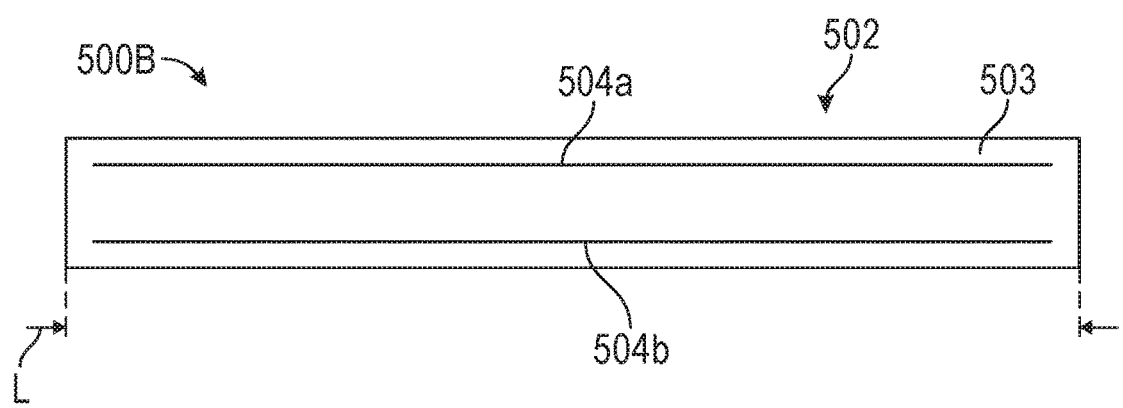
FIG. 5B illustrates a front view of an implant, in accordance with at least one example of this disclosure.

FIG. 5B illustrates a front view of an implant 500B, in accordance with at least one example of this disclosure. The implant 500B can include a ribbon 502, a first wire 504a and a second wire 504b.

The implant 500B can be similar to the implants discussed above, except that the implant 500B can include the first wire 504a and the second wire 504b, where each of the first wire 504a and the second wire 504b can be connected to the ribbon 502 and can extend along a length L of an elongate body 503 of the ribbon 502. The wires 504 can each be relatively straight along the length L of the ribbon 502. The second wire 504b can be substantially parallel to the first wire 504a. Though two wires 504 are shown in FIG. 5B, more wires can be used, such as 3, 4, 5, 6, 7, 8, 9, 10, 15, 20, or the like wires.

Figure 5C:
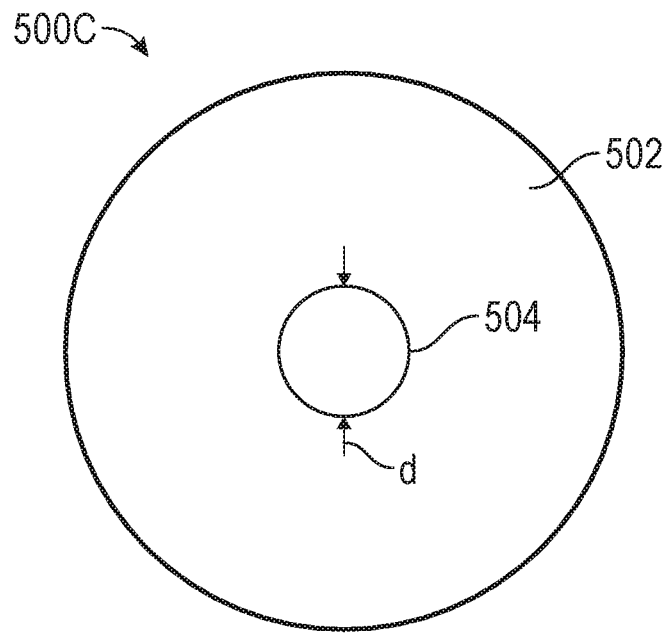
FIG. 5C illustrates a cross-sectional view of an implant, in accordance with at least one example of this disclosure.

FIG. 5C illustrates a cross-sectional view of an implant 500C, in accordance with at least one example of this disclosure. The implant 500C can include a body 502 and a wire 504. Also shown in FIG. 5C is a diameter d of the wire 504.

The implant 500C can be similar to those discussed above, except that the body 502 can be a bioresorbable layer surrounding the wire 504. The shape of the implant 500C can help to fill relatively larger cavities. In some examples, the diameter d of the wire 504 can be between 0.01 millimeters and 5 millimeters. In some examples, the diameter d of the wire 504 can be between 0.05 millimeters and 2 millimeters.

Figure 5D:
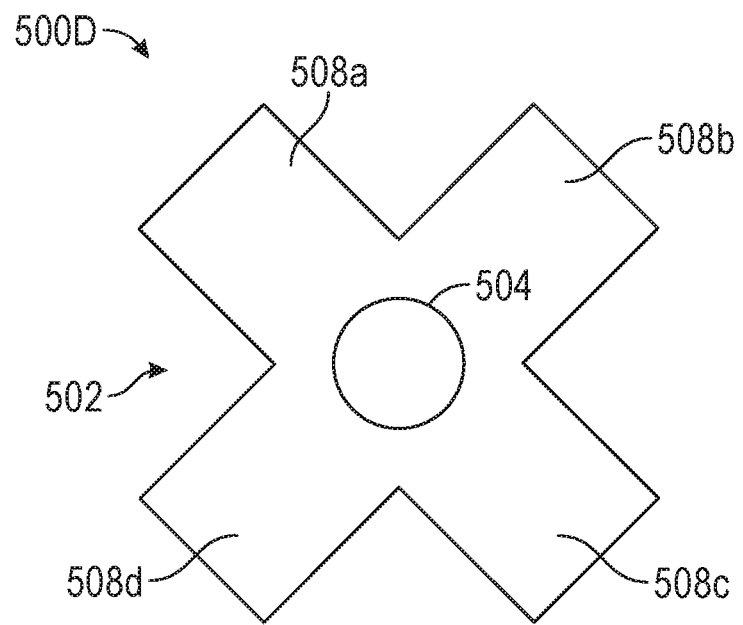
FIG. 5D illustrates a cross-sectional view of an implant, in accordance with at least one example of this disclosure.

FIG. 5D illustrates a cross-sectional view of an implant 500D, in accordance with at least one example of this disclosure. The implant 500D can include a body 502 and a wire 504. The body 502 can include arms 508a-508d (collectively referred to as arms 508).

The implant 500D can be similar to the implant 500C discussed above, except that the body 502 can have a cross-sectional shape of a plus or an X, where the arms 508 can extend radially outward from the wire 504. The shape of the implant 500D can help to fill relatively larger cavities, while the arms 508 can have a relatively small thickness, which can help to reduce a time required for resorption of the body 502.

Though the implants 100-500 discussed above are discussed as being configured for implantation into a cavity of a breast, the implants can be configured for implantation into any cavity to act as a fiducial or marker for the purposes of imaging and/or targeted radiation therapy. For example, the implants can be configured for implantation into bone.

Though wires 104-504 are discussed as being wires, the fiducial elements can have other elongate radiopaque shapes, such as a ribbon shape (rectangular prism), a triangular prism shape, a hexagonal prism shape, an octagonal prism shape, or the like. In some examples the wires 104-504 can be of a single strand. In other examples, the wires can be made of multiple woven strands. In some examples, the wires 104-504 can be of a single extruded piece. In other examples, the wires 104-504 can be made of several connected pieces (or several disconnected pieces).

In some examples, the wire can be of the shape of multiple disconnected loops where each loop has no ends. That is, a plurality of wires in the shape of loops can be connected to the body of the ribbon, which can reduce sharp ends of the radiopaque wire, and can simplify removal of the wires, when such a procedure is necessary.

Any of the ribbons 200, 300, 400, or 500 or methods regarding such ribbons discussed above can be used in any procedure where a surgical procedure leaves a crater, dent, divot, or recessed cavity in the body such as the removal of tumors, cysts, lipomas, or dermoid cysts, or the like.

Figure 6A:
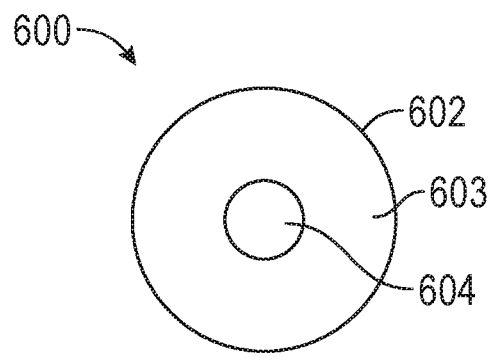
FIG. 6A illustrates a front view of an implant, in accordance with at least one example of this disclosure.
Figure 6B:
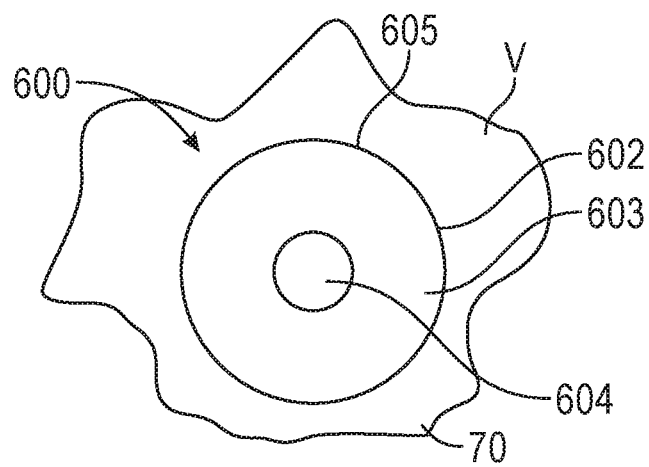
FIG. 6B illustrates a front view of a cavity filled with an implant, in accordance with at least one example of this disclosure.

FIG. 6A illustrates a front view of an implant 600, in accordance with at least one example of this disclosure. The implant 600 can include a body 602 and a marker 604. The body 602 can be formed of a hydrogel 603, as discussed in further detail below. FIG. 6B shows the implant 600 in a cavity 70. FIGS. 6A and 6B are discussed together below.

The implant 600 can generally be an implant configured for implantation into a human body, such as the cavity 56 of the breast 50 of FIG. 1 or the cavity 70 of FIG. 6B. However, the implant 600 can be implantable into cavities in a variety of locations in a body. The hydrogel 603 that forms the body 602 (or most of the body 602) can be made of biocompatible materials, such as a non-bioabsorbable (or non-bioresorbable) hydrogel. The hydrogel 603 can be one or more of a homopolymer, a copolymer, a semi-interpenetrating network, an interpenetrating network, and a self-assembling peptide system. The hydrogel 603 can be radiolucent for observation or identification of the radiopaque markers 604.

The hydrogel can be degradable or non-degradable and can be a natural or synthetic polymer network that is hydrophilic and can absorb a high amount of water. The hydrogel can be a solid or porous hydrogel/polymer and can be made from any non-biodegradable polymer. A non-biodegradable polymer having mechanical properties that can be controlled separately by varying the polymer concentration and/or the method of polymerization can be used, including one or more of polyvinyl pyrrolidone, polyacrylamide, polyethylene glycol, or polyurethane. In some examples, polyvinyl alcohol (PVA) can be used. The hydrogel modulus properties can be controlled separately by varying polymer and water concentrations or a method of gelation such as freezing and thawing. In its dehydrated form, a solid hydrogel can change in shape, size, and stiffness providing shelf-life stability. Upon rehydration, the hydrogel can swell to its full size.

The body 602 of the implant 602 can be a generally flexible member having a shape of a sphere. The body 602 can have other shapes in other examples, such as an ovoid, an oblate spheroid, a prolate spheroid, a cube, a dodecahedron, a icosahedron, or the like. Use of a rounded shape can help to reduce palpability of the implant 600 following implantation in a breast cavity. The body 602 can be non-bioabsorbable such that the implant 600 can fill a volume v of the breast cavity 70 following the lumpectomy to help maintain the shape of the of the breast following the lumpectomy.

The marker 604 can be made of biocompatible and radiopaque materials such as one or more of titanium, titanium alloys, polyether ether ketone, a stainless-steel alloy, a cobalt-chromium alloy, or the like. The marker 604 can have a spherical shape and can be configured to act as a fiducial or marker for the cavity, such as by being radiopaque (visible in radiographic images) to mark the cavity after implantation of the implant 600. The marker 604 can be in a fixed location within the body 602 or can be free to move within the body 602.

As shown in FIG. 6B, the body 602 and the radiopaque marker 604 together can be configured to fill at least a portion of the cavity 70 to help fill the cavity 70 after implantation. Once implanted within the cavity 70, the body 602 and the radiopaque marker 604 can move together with respect to the cavity 70 or with the cavity. The hydrogel 603 forming at least a portion of the body 602 can be made of a hydrogel having a modulus of elasticity similar to a modulus of elasticity of human subcutaneous breast tissue. For example, the modulus of elasticity of the hydrogel 603 can be between 0.5 and 25 kilopascals. The modulus of elasticity of the hydrogel 603 can be between 5 and 20 kilopascals. The modulus of elasticity of the hydrogel 603 can be between 10 and 15 kilopascals. By using a hydrogel with qualities similar to that of human breast tissue, discomfort caused by the implant 600 can be reduced and palpability of the implant 600 can be reduced.

FIG. 6B also shows an outer layer 605 of the body 602 that can be a dehydrated layer of hydrogel. Following implantation of the implant 600 into the cavity 70, the dehydrated layer 605 can absorb liquid (the liquid can be of the cavity 70 or inserted therein) to expand within the cavity 70. Such expansion of the outer layer 605 and therefore the implant 600 can help to create a hemostatic environment, which can help to reduce bleeding or hematomas within the cavity 70.

Figure 6C:
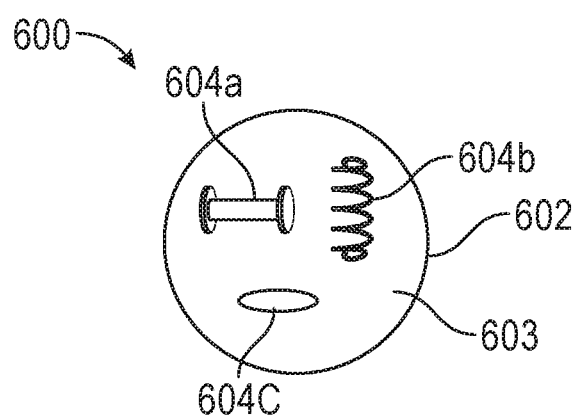
FIG. 6C illustrates a front view of an implant, in accordance with at least one example of this disclosure.

FIG. 6C illustrates a front view of an implant 600, in accordance with at least one example of this disclosure. The implant 600 can be similar to the implant of FIGS. 6A and 6B; FIG. 6C shows that the implant 600 can include multiple markers 604 and can include markers of various shapes. For example, a marker 604a can have a dumbbell shape, a marker 604b can have a coil shape, a helix shape, or a compression spring shape, and the marker 604c can have a ovoid shape. The marker 604 can be of other shapes in other examples.

In some examples, markers within each implant can have a unique shape to allow for individual tracking of implants following implantation. For example, a kit can be provided including several implants, where each implant has a marker in the shape of a number, a letter, or another shape unique to the kit or set of implants.

Figure 6D:
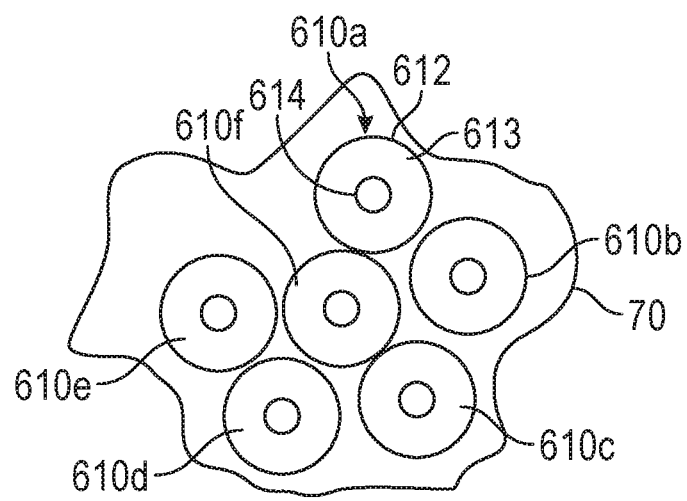
FIG. 6D illustrates a front view of a cavity filled with an implant, in accordance with at least one example of this disclosure.

FIG. 6D illustrates a front view of the cavity 70 filled with implants 610, in accordance with at least one example of this disclosure. The implant 610 can be similar to the implant 600 discussed above, where the implant 610 can be relatively smaller than the implant 600, as discussed in further detail below. The implant 610 can include a body 612 of hydrogel 613 and a marker 614, which can be similar to the body 602, the hydrogel 603, and the marker 604 of the implant 600, respectively.

By using the implant 610 that has a size that is relatively smaller than the implant 600 with respect to the cavity 70, the implants 610a, 610b, 610c, 610d, 610e, and 610f can be used to fill the cavity 70 and to help match a shape and volume of the cavity 70. Use of multiple implants 610 can also allow the implants 610 to move easier within the cavity 70 which can allow the implants to maintain the shape of the cavity 70 as the surrounding tissue moves.

Figure 6E:
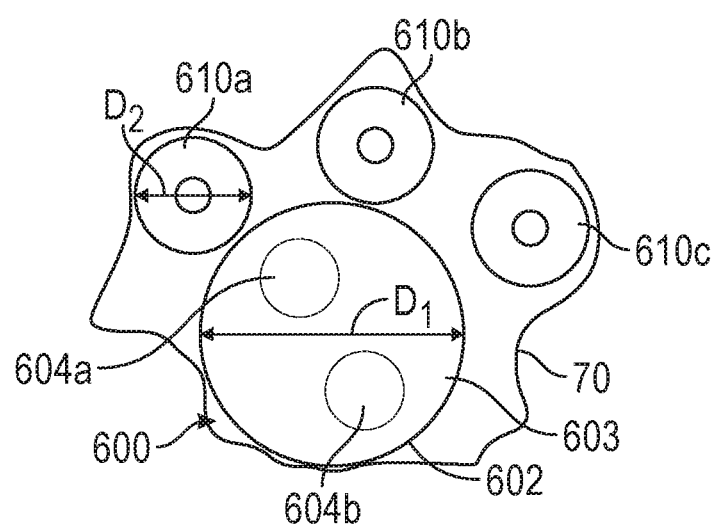
FIG. 6E illustrates a front view of a cavity filled with an implant, in accordance with at least one example of this disclosure.

FIG. 6E illustrates a front view of the cavity 70 filled with the implant 600 and the implants 610. FIG. 6E shows that the implant 600 can have a diameter D1 that can be larger than a diameter D2 of the implants 610. By using one of the implant 600 and multiple of the implants 610, the cavity 70 can be relatively quickly filled by the implant 600 and the irregular shape of the cavity 70 can be filled by the implants 610a-610c allowing relatively few implants to be used while the combination of implants can still conform to the shape of, or fill, the cavity 70. FIG. 6E also shows that one or more of the implants 600 and 610 can include multiple markers 604a and 604b, which can help to distinguish types of implants following implantation.

FIG. 7A illustrates a front view of a lumpectomy procedure, in accordance with at least one example of this disclosure. FIG. 7B illustrates a side view of a lumpectomy procedure, in accordance with at least one example of this disclosure. FIGS. 7A and 7B are discussed together below.

FIGS. 7A and 7B show a human breast 50 and a cavity 56. FIGS. 7A and 7B also show an inserter assembly 700 and implants 610a, 610b, and 610c.

The implants 610 can be similar to the implants 600 and 610 discussed above. The inserter assembly 700 can include an introducer 702, which can be an elongate tube that can be flexible or can be rigid. The introducer 702 can be configured to extend from a cavity to external to the tissue, as discussed below. The introducer 702 can be made of one or more of polymers, metals, or the like. The inserter assembly 700 can optionally include multiple introducers with multiple internal diameters for insertion of implants of varying diameters. In some examples, the introducer 702 can have an internal diameter sufficiently large to accommodate insertion of implants of every size included in an assembly or kit of implants (e.g., implants 600 and 610).

In operation of some examples, an incision 72 can be created around an areola 74 of the breast 50 for removal of the tumor. The incision can be located at any other location of the breast. Following removal of the tumor, the implants 610 can be placed into the cavity 70 by hand, for example, when the cavity 56 is near the incision 72. When the cavity 56 is distant from the incision, such as shown in FIGS. 7A and 7B, or when the cavity 56 is tunneled, the introducer 702 can be used to insert the implants 610. A biocompatible surgical lubricant can optionally be applied to an external surface of the introducer 702 to reduce friction between the introducer 702 and breast tissue. A biocompatible surgical lubricant can also optionally be, applied to an internal surface of the introducer 702 (such as via injection) to reduce friction between the introducer 702 and implants 610 during insertion of the implants 610.

Following lubrication, the introducer 702 can be inserted through the incision 72 until it reaches the cavity 56. The implants 610 can be inserted into a proximal end of the introducer 702 where each of the implants 610 can be guided by the introducer 702 into the cavity 56. The implants 610 can be added, for example one at a time, until the cavity is filled or is sufficiently filled, as determined by a surgeon.

Figure 7C:
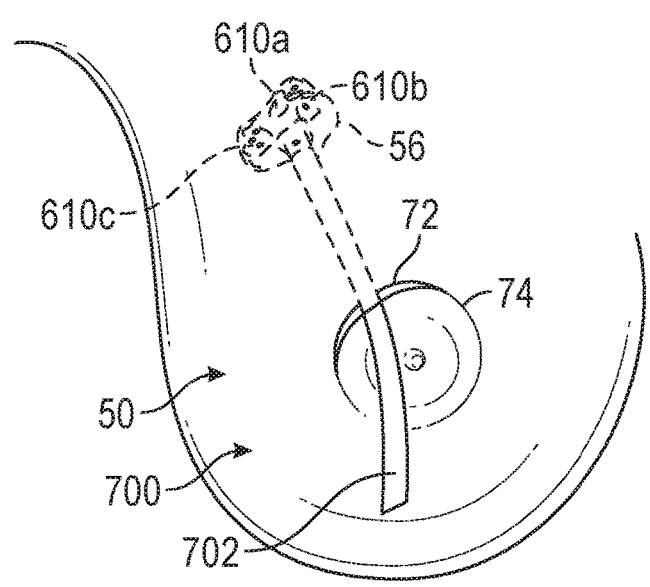
FIG. 7C illustrates a perspective view of an implant assembly, in accordance with at least one example of this disclosure.
Figure 7C:
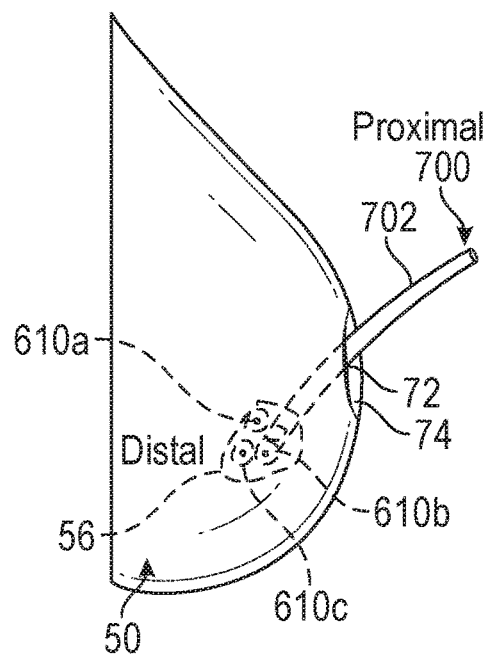
Figure 7C:
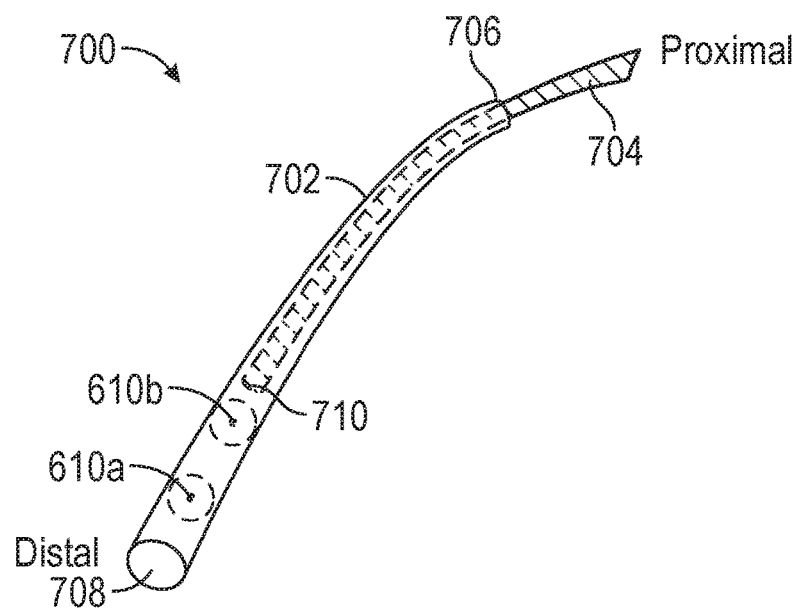

FIG. 7C shows that the implant assembly 700 can include a stylet 704, which can be a rigid or semi-rigid elongate member. FIG. 7C also shows that the introducer can include a proximal opening 706 and the distal opening 708.

The stylet can have an outer diameter smaller than an inner diameter of the introducer 702 such that the stylet 704 can be inserted into a proximal opening 706 of the introducer 702 and the stylet 704 can be extended into the introducer 702 along a length of the introducer 702. The stylet 704 can include a blunt end 710 configured to engage implants, such as the implants 610a and 610b within the introducer 702. In some examples, the stylet 704 can have a length that is longer than a length of the introducer 702.

During operation, following insertion of the introducer 702, it may be desired to guide the implants 610a and 610b into the cavity 56 through the introducer, such as if the implants 610a and 610h cease moving through the introducer 702 via the force of gravity alone. The stylet 704 can be inserted into the proximal opening 706 of the introducer 702 to engage the implants 610a and 610b with the blunt end 710 of the stylet 704 to urge or three the implants 610 distally through the introducer 702, out of the distal opening 708, and into the cavity 56. Following placement of the implants 610 within the cavity, the introducer 702 and the stylet 704 can be removed from the cavity 56 and incision 72 and the openings can be closed in standard surgical fashion.

Though the methods and systems herein are discussed above with respect to lumpectomies performed in human breasts, the implants, systems, and methods can be used in any other procedure where a surgical procedure leaves a crater, dent, divot, or recessed cavity in the body such as the removal of tumors, cysts, lipomas, or dermoid cysts, or the like.

NOTES AND EXAMPLES

The following, non-limiting examples, detail certain aspects of the present subject matter to solve the challenges and provide the benefits discussed herein, among others.

Example 1 is an implant comprising: a ribbon defining a flexible elongate body, the ribbon comprised of a bioresorbable material; and a radiopaque wire connected to the ribbon and extending along a length of the ribbon, the ribbon and the radiopaque wire configured for implantation in a body cavity to mark the cavity in a radiographic image of the cavity.

In Example 2, the subject matter of Example 1 optionally includes wherein the radiopaque wire is configured to be visible in the radiographic image to mark the cavity in the radiographic image of the cavity after implantation of the implant and after resorption of the ribbon.

In Example 3, the subject matter of any one or more of Examples 1-2 optionally include wherein the ribbon and the radiopaque wire are configured to move together with respect to the cavity and within the cavity after implantation.

In Example 4, the subject matter of Example 3 optionally includes wherein a first end of the ribbon and a first end of the radiopaque wire are configured to move with respect to a second end of the ribbon and a second end of the radiopaque wire within the cavity after implantation in response to forces applied to the cavity.

In Example 5, the subject matter of any one or more of Examples 1-4 optionally include wherein the ribbon and the radiopaque wire together are configured to fill at least a portion of the cavity to hold the cavity open after implantation.

In Example 6, the subject matter of any one or more of Examples 1-5 optionally include wherein the ribbon and the radiopaque wire together are positionable to fill the cavity when the cavity has an irregular shape.

In Example 7, the subject matter of any one or more of Examples 1-6 optionally include a second radiopaque wire connected to the ribbon and extending along the length of the ribbon, the second radiopaque wire substantially parallel to the radiopaque wire.

In Example 8, the subject matter of any one or more of Examples 1-7 optionally include a second radiopaque wire connected to the ribbon and extending along a width of the ribbon, the second radiopaque wire substantially orthogonal to the radiopaque wire.

In Example 9, the subject matter of any one or more of Examples 1-8 optionally include wherein the ribbon is a mesh.

In Example 10, the subject matter of any one or more of Examples 1-9 optionally include wherein the ribbon defines a width smaller than the length, and a thickness smaller than the width.

In Example 11, the subject matter of Example 10 optionally includes wherein the width is between 0.1 centimeters and 3 centimeters.

In Example 12, the subject matter of Example 11 optionally includes wherein a diameter of the radiopaque wire is between 0.05 millimeters and 3 millimeters.

In Example 13, the subject matter of any one or more of Examples 1-12 optionally include wherein the radiopaque wire is comprised of titanium, polyether ether ketone, a stainless-steel alloy, and a cobalt chromium alloy, or a combination thereof.

In Example 14, the subject matter of any one or more of Examples 1-13 optionally include wherein the ribbon is comprised of a collagen, a glycosaminoglycan, a starch, a silk, an alginate, a chitin, a chitosan, a polylactic acid, a polyglycolic acid, a polyanhydride, a polycaprolactone, a poly(hydroxbutyrate), a poly(hydroxyvalerate), or a combination thereof.

In Example 15, the subject matter of any one or more of Examples 1-14 optionally include wherein the radiopaque wire extends along an entirety of the length of the ribbon.

Example 16 is a method of implanting a marker comprising: selecting an implant length based on a size of a cavity; and inserting the implant into the cavity to at least partially fill the cavity, the implant including a ribbon defining a flexible elongate body comprised of a bioresorbable material, and the implant including a radiopaque wire connected to the ribbon and extending along a length of the ribbon.

In Example 17, the subject matter of Example 16 optionally includes acquiring a radiographic image of the cavity showing the radiopaque wire within the cavity.

In Example 18, the subject matter of any one or more of Examples 16-17 optionally include directing radiation at the radiopaque wire to deliver radiation to the cavity.

In Example 19, the subject matter of any one or more of Examples 16-18 optionally include positioning the implant within the cavity to substantially fill a volume of the cavity.

In Example 20, the subject matter of Example 19 optionally includes wherein the cavity has an irregular shape.

In Example 21, the subject matter of any one or more of Examples 16-20 optionally include wherein the radiopaque wire is configured to be visible in a radiographic image to mark the cavity after implantation of the implant and after resorption of the ribbon.

In Example 22, the subject matter of any one or more of Examples 16-21 optionally include wherein the ribbon and the radiopaque wire are configured to flex within the cavity after implantation.

Example 23 is a method of implanting a marker comprising: trimming a length of the implant; and inserting the implant into a cavity to at least partially fill the cavity, the implant including a ribbon defining a flexible elongate body comprised of a bioresorbable material, and the implant including a radiopaque wire connected to the ribbon and extending along a length of the ribbon.

In Example 24, the subject matter of Example 23 optionally includes selecting the implant length based on a size of a cavity prior to trimming the length.

In Example 25, the subject matter of any one or more of Examples 23-24 optionally include acquiring a radiographic image of the cavity showing the radiopaque wire within the cavity.

In Example 26, the subject matter of any one or more of Examples 23-25 optionally include directing radiation at the radiopaque wire to deliver radiation to the cavity.

In Example 27, the subject matter of any one or more of Examples 23-26 optionally include positioning the implant within the cavity to substantially fill a volume of the cavity.

Example 28 is an implant comprising: a flexible elongate body, the body comprised of a bioresorbable material; and a radiopaque wire connected to the body and extending along a length of the body, the body and the radiopaque wire configured for implantation in a body cavity to mark the cavity in a radiographic image of the cavity.

In Example 29, the subject matter of Example 28 optionally includes wherein the radiopaque wire is configured to be visible in the radiographic image to mark the cavity in the radiographic image of the cavity after implantation of the implant and after resorption of the body.

In Example 30, the subject matter of Example 29 optionally includes wherein the body and the radiopaque wire are configured to move together with respect to the cavity and within the cavity after implantation.

In Example 31, the subject matter of Example 30 optionally includes wherein a first end of the body and a first end of the radiopaque wire are configured to move with respect to a second end of the body and a second end of the radiopaque wire within the cavity after implantation in response to forces applied to the cavity.

In Example 32, the subject matter of any one or more of Examples 29-31 optionally include wherein the body and the radiopaque wire together are configured to fill at least a portion of the cavity to hold the cavity open after implantation.

In Example 33, the subject matter of any one or more of Examples 29-32 optionally include wherein the body and the radiopaque wire together are positionable to fill the cavity when the cavity has an irregular shape.

In Example 34, the subject matter of any one or more of Examples 29-33 optionally include a second radiopaque wire connected to the body and extending along the length of the body, the second radiopaque wire substantially parallel to the radiopaque wire.

In Example 35, the subject matter of any one or more of Examples 29-34 optionally include a second radiopaque wire connected to the body and extending along a width of the body, the second radiopaque wire substantially orthogonal to the radiopaque wire.

In Example 36, the subject matter of any one or more of Examples 29-35 optionally include wherein the body is a mesh.

In Example 37, the subject matter of any one or more of Examples 29-36 optionally include wherein the body defines a width smaller than the length, and a thickness smaller than the width.

In Example 38, the subject matter of Example 37 optionally includes wherein the width is between 0.1 centimeters and 3 centimeters.

In Example 39, the subject matter of Example 38 optionally includes wherein a diameter of the radiopaque wire is between 0.05 millimeters and 3 millimeters.

In Example 40, the subject matter of any one or more of Examples 29-39 optionally include wherein the radiopaque wire is comprised of titanium, polyether ether ketone, a stainless-steel alloy, and a cobalt chromium alloy, or a combination thereof.

In Example 41, the subject matter of any one or more of Examples 29-40 optionally include wherein the ribbon is comprised of a collagen, a glycosaminoglycan, a starch, a silk, an alginate, a chitin, a chitosan, a polylactic acid, a polyglycolic acid, a polyanhydride, a polycaprolactone, a poly(hydroxbutyrate), a poly(hydroxyvalerate), or a combination thereof.

In Example 42, the subject matter of any one or more of Examples 29-41 optionally include wherein the body is cylindrical.

In Example 43, the subject matter of any one or more of Examples 29-42 optionally include wherein the body has cross sectional X shape.

Example 44 is an implant comprising: a flexible body made of a non-bioresorbable hydrogel material; and a radiopaque marker located within the flexible body, the body and the radiopaque marker configured for implantation in a body cavity to mark the cavity in a radiographic image of the cavity.

In Example 45, the subject matter of Example 44 optionally includes wherein the radiopaque marker is configured to be visible in the radiographic image to mark the cavity in the radiographic image of the cavity after implantation of the implant.

In Example 46, the subject matter of any one or more of Examples 44-45 optionally include wherein the flexible body and the radiopaque marker are configured to move together with respect to the cavity and within the cavity after implantation.

In Example 47, the subject matter of any one or more of Examples 44-46 optionally include wherein the flexible body and the radiopaque marker together are configured to fill at least a portion of the cavity to hold the cavity open after implantation.

In Example 48, the subject matter of any one or more of Examples 44-47 optionally include wherein the flexible body has a geometric shape of a sphere.

In Example 49, the subject matter of any one or more of Examples 44-48 optionally include wherein the flexible body is made of a hydrogel having a modulus of elasticity similar to a modulus of elasticity of human subcutaneous breast tissue.

In Example 50, the subject matter of Example 49 optionally includes wherein a modulus of elasticity of the hydrogel of the first body and the second body is between 0.5 and 25 kilopascals.

In Example 51, the subject matter of any one or more of Examples 44-50 optionally include wherein the radiopaque marker is made of titanium, polyether ether ketone, a stainless-steel alloy, and a cobalt chromium alloy, or a combination thereof.

In Example 52, the subject matter of any one or more of Examples 44-51 optionally include a second radiopaque marker located within the flexible body, the second radiopaque marker, together with the flexible body and the radiopaque marker, configured for implantation in the body cavity to mark the cavity in a radiographic image of the cavity.

Example 53 is an implant assembly comprising: a first implant comprising: a first body made of a flexible and non-bioresorbable hydrogel material, the first body having a shape of a sphere defining a first diameter; and a first marker located within the first body, the first marker made of a radiopaque material, and the first body and the first marker configured for implantation in a body cavity to mark the cavity in a radiographic image of the cavity; and a second implant comprising: a second body made of the flexible and non-bioresorbable hydrogel material, the second body having a shape of a sphere defining a second diameter different from the first diameter; and a second marker located within the second body, the second marker made of a radiopaque material, and the second body and the second marker configured for implantation in the body cavity to mark the cavity in a radiographic image of the cavity.

In Example 54, the subject matter of Example 53 optionally includes wherein the second diameter is smaller than the first diameter.

In Example 55, the subject matter of any one or more of Examples 53-54 optionally include wherein the second diameter is less than half of the first diameter.

In Example 56, the subject matter of any one or more of Examples 53-55 optionally include wherein the first implant and the second implant are positionable to fill the cavity when the cavity has an irregular shape.

In Example 57, the subject matter of any one or more of Examples 53-56 optionally include wherein the modulus of elasticity of the hydrogel of the first body and the second body is between 0.5 and 25 kilopascals.

In Example 58, the subject matter of any one or more of Examples 53-57 optionally include wherein the first body and the second body have geometric shapes of spheres.

Example 59 is an implant assembly comprising: a plurality of first implants, each of the first implants comprising: a first body made of a flexible and non-bioresorbable hydrogel material, the first body having a shape of a sphere defining a first diameter; and a first marker located within the first body, the first marker made of a radiopaque material, and the first body and the first marker configured for implantation in a body cavity to mark the cavity in a radiographic image of the cavity; and a plurality of second implants, each of the second implants comprising: a second body made of the flexible and non-bioresorbable hydrogel material, the second body having a shape of a sphere defining a second diameter different from the first diameter; and a second marker located within the second body, the second marker made of a radiopaque material, and the second body and the second marker configured for implantation in the body cavity to mark the cavity in a radiographic image of the cavity.

In Example 60, the subject matter of Example 59 optionally includes wherein a quantity of first implants and a quantity of second implants is selectable to fill the cavity when the cavity has an irregular shape.

In Example 61, the subject matter of Example 60 optionally includes wherein the second diameter is smaller than the first diameter.

In Example 62, the subject matter of any one or more of Examples 60-61 optionally include wherein the second diameter is less than half of the first diameter.

In Example 63, the subject matter of any one or more of Examples 59-62 optionally include wherein a modulus of elasticity of the hydrogel of the first body and the second body is between 0.5 and 25 kilopascals.

Example 64 is an implant assembly comprising: an implant selectable from a plurality of implants, the implant comprising: a body made of a flexible and non-bioresorbable hydrogel, the body having a shape of a sphere; and a marker located within the body, the marker made of a radiopaque material, and the body and the marker configured for implantation in a breast cavity to mark the cavity in a radiographic image of the cavity; and an introducer comprising an elongate tube insertable into the breast cavity and configured to receive the implant therethrough to guide the implant into the breast cavity.

In Example 65, the subject matter of Example 64 optionally includes a stylet insertable into the introducer and configured to engage the implant to position the implant within the breast cavity.

In Example 66, the subject matter of Example 65 optionally includes wherein the stylet has a length that is longer than a length of the introducer.

In Example 67, the subject matter of any one or more of Examples 65-66 optionally include wherein the plurality of implants each have a shape of a sphere.

In Example 68, the subject matter of Example 67 optionally includes wherein a first quantity of the plurality of implants define a first diameter and wherein a second quantity of the plurality of implants define a second diameter that is smaller than the first diameter.

In Example 69, the subject matter of any one or more of Examples 64-68 optionally include wherein the body is made of a hydrogel having a modulus of elasticity similar to a modulus of elasticity of human subcutaneous breast tissue.

In Example 70, the subject matter of any one or more of Examples 64-69 optionally include a dehydrated hydrogel layer located on and connected to an exterior surface of the body, the dehydrated hydrogel layer configured to expand within the breast cavity upon implantation thereof.

Example 71 is an implant comprising: a flexible body made of a non-bioresorbable hydrogel material; and a radiopaque marker located at least partially within the flexible body, the body and the radiopaque marker to mark a body cavity in a radiographic image of the cavity following implantation of the implant within in the body cavity.

In Example 72, the subject matter of Example 71 optionally includes wherein the radiopaque marker radiographically marks the cavity after implantation of the implant.

In Example 73, the subject matter of any one or more of Examples 71-72 optionally include wherein the flexible body and the radiopaque marker are configured to move together with respect to the cavity and within the cavity after implantation.

In Example 74, the subject matter of any one or more of Examples 71-73 optionally include wherein the flexible body hearing the radiopaque marker is dimensioned to fill at least a portion of the cavity.

In Example 75, the subject matter of any one or more of Examples 71-74 optionally include wherein the flexible body has a geometric shape of a sphere.

In Example 76, the subject matter of any one or more of Examples 71-75 optionally include wherein the flexible body is made of a hydrogel having a modulus of elasticity similar to a modulus of elasticity of human subcutaneous breast tissue.

In Example 77, the subject matter of Example 76 optionally includes wherein the modulus of elasticity of the hydrogel of the flexible body is between 0.5 and 25 kilopascals.

In Example 78, the subject matter of any one or more of Examples 71-77 optionally include wherein the radiopaque marker is made of titanium, polyether ether ketone, a stainless-steel alloy, and a cobalt chromium alloy, or a combination thereof.

In Example 79, the subject matter of any one or more of Examples 71-78 optionally include a second radiopaque marker located within the flexible body, the second radiopaque marker, together with the flexible body and the radiopaque marker, to mark the body cavity in a radiographic image of the cavity following implantation of the implant within the body cavity.

Example 80 is an implant assembly comprising: a first implant comprising: a first body made of a flexible and non-bioresorbable hydrogel material, the first body having a first shape; and a first marker located at least partially within the first body, the first marker made of a radiopaque material, and the first body and the first marker implantable in a body cavity to mark the cavity in a radiographic image of the cavity; and a second implant comprising: a second body made of the flexible and non-bioresorbable hydrogel material, the second body having a second shape; and a second marker located at least partially within the second body, the second marker made of a radiopaque material, and the second body and the second marker implantable in the body cavity to mark the cavity in a radiographic image of the cavity, wherein the first shape and the second shape are the same shape or are different shapes, and wherein the first shape and the second shape are the same size or are different sizes.

In Example 81, the subject matter of Example 80 optionally includes wherein the first body and the second body have geometric shapes of spheres and wherein the first body defines a first diameter and the second body defines a second diameter.

In Example 82, the subject matter of Example 81 optionally includes wherein the second diameter is smaller than the first diameter.

In Example 83, the subject matter of any one or more of Examples 81-82 optionally include wherein the second diameter is less than half of the first diameter.

In Example 84, the subject matter of any one or more of Examples 80-83 optionally include wherein the first implant and the second implant are positionable to fill the cavity when the cavity has an irregular shape.

In Example 85, the subject matter of any one or more of Examples 80-84 optionally include wherein the modulus of elasticity of the hydrogel of the first body and the second body is between 0.5 and 25 kilopascals.

Example 86 is an implant assembly comprising: an implant comprising one or more selectable implant bodies, the implant comprising: an implant body made of a flexible and non-bioresorbable hydrogel; and a marker located within the implant body, the marker made of a radiopaque material, the implant body bearing the marker being implantable in a breast cavity to mark the cavity in a radiographic image of the cavity; and an introducer comprising an elongate tube insertable into a body cavity and operable to receive the implant body therethrough to guide the implant body into the body cavity.

In Example 87, the subject matter of Example 86 optionally includes a stylet insertable into the introducer and operable to engage the implant to position the implant body within the body cavity.

In Example 88, the subject matter of Example 87 optionally includes wherein the stylet has a length that is longer than a length of the introducer.

In Example 89, the subject matter of any one or more of Examples 86-88 optionally include wherein the implant comprises a plurality of implant bodies selectable from the plurality of implant bodies, wherein a first quantity of the plurality of implant bodies define a first diameter and wherein a second quantity of the implant bodies define a second diameter that is smaller than the first diameter.

In Example 90, the subject matter of any one or more of Examples 86-89 optionally include a dehydrated hydrogel layer located on and connected to an exterior surface of the implant body, the dehydrated hydrogel layer to expand within the body cavity following implantation thereof.

Example 91 is a method of implanting a plurality of implants in a body cavity, the method comprising: selecting an implant from a plurality of implants, the implant including a body made of a flexible and non-bioresorbable hydrogel and including a radiopaque marker located at least partially within the body; inserting an introducer defining an elongate tube into the body cavity; and inserting the implant into the body cavity using the introducer.

In Example 92, the subject matter of Example 91 optionally includes inserting a stylet into the introducer to engage the implant to position the implant within the body cavity.

In Example 93, the subject matter of any one or more of Examples 91-92 optionally include selecting a second implant from the plurality of implants; and inserting the second implant into the body cavity using the introducer.

In Example 94, the subject matter of Example 93 optionally includes wherein the first implant and the second implant are of different sizes.

In Example 95, the subject matter of any one or more of Examples 93-94 optionally include wherein the first implant and the second implant are spheres having different diameters.

In Example 96, the apparatuses or method of any one or any combination of Examples 1-95 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An implant assembly comprising:
   a first implant comprising:
      a first body made of a flexible and non-bioresorbable hydrogel material, the first body having a first shape; and
      a first marker located at least partially within the first body, the first marker made of a radiopaque material, and the first body and the first marker implantable in a body cavity to mark the cavity in a radiographic image of the cavity; and
   a second implant comprising:
      a second body made of the flexible and non-bioresorbable hydrogel material, the second body having a second shape; and
      a second marker located at least partially within the second body, the second marker made of a radiopaque material, and the second body and the second marker implantable in the body cavity to mark the cavity in a radiographic image of the cavity,
      wherein the first shape and the second shape are the same shape or are different shapes,
      wherein the first shape and the second shape are the same size or are different sizes,
      wherein the first body and the second body have geometric shapes of spheres and wherein the first body defines a first diameter and the second body defines a second diameter, and
      wherein the second diameter is smaller than the first diameter.

2. The implant assembly of claim 1, wherein the second diameter is less than half of the first diameter.

3. The implant assembly of claim 1, wherein the first implant and the second implant are positionable to fill the cavity when the cavity has an irregular shape.

4. The implant assembly of claim 1, wherein a modulus of elasticity of the hydrogel of the first body and the second body is between 0.5 and 25 kilopascals.

5. An implant assembly comprising:
   an implant comprising one or more selectable implant bodies, the implant comprising:
      an implant body made of a flexible and non-bioresorbable hydrogel; and
      a marker located within the implant body, the marker made of a radiopaque material, the implant body bearing the marker being implantable in a breast cavity to mark the cavity in a radiographic image of the cavity; and
      an introducer comprising an elongate tube insertable into a body cavity and operable to receive the implant body therethrough to guide the implant body into the body cavity;
      wherein the implant comprises a plurality of implant bodies selectable from the plurality of implant bodies, wherein a first quantity of the plurality of implant bodies define a first diameter and wherein a second quantity of the implant bodies define a second diameter that is smaller than the first diameter.

6. The implant assembly of claim 5, further comprising:
   a stylet insertable into the introducer and operable to engage the implant to position the implant body within the body cavity.

7. The implant assembly of claim 6, wherein the stylet has a length that is longer than a length of the introducer.

8. The implant of claim 5, further comprising:
   a dehydrated hydrogel layer located on and connected to an exterior surface of the implant body, the dehydrated hydrogel layer to expand within the body cavity following implantation thereof.

9. An implant assembly comprising:
   a first implant comprising:
      a first body made of a flexible and non-bioresorbable hydrogel material, the first body having a first shape, and the first body defining a first diameter; and a first marker located at least partially within the first body, the first marker made of a radiopaque material, and the first body and the first marker implantable in a body cavity to mark the cavity in a radiographic image of the cavity; and a second implant comprising:

a second body made of the flexible and non-bioresorbable hydrogel material, the second body having a second shape, the first body and the second body having geometric shapes of spheres, and the second body defining a second diameter that is smaller than the first diameter; and a second marker located at least partially within the second body, the second marker made of a radiopaque material, and the second body and the second marker implantable in the body cavity to mark the cavity in a radiographic image of the cavity.

10. The implant assembly of claim 9, wherein the second diameter is less than half of the first diameter.

11. The implant assembly of claim 9, wherein the first implant and the second implant are positionable to fill the cavity when the cavity has an irregular shape.

12. The implant assembly of claim 9, wherein a modulus of elasticity of the hydrogel of the first body and the second body is between 0.5 and 25 kilopascals.

* * * * *